United States Patent [19]

Ismail et al.

[11] Patent Number: 4,755,472

[45] Date of Patent: Jul. 5, 1988

[54] STABLE COMPOSITION FOR THE DETERMINATION OF PEROXIDATIVELY ACTIVE SUBSTANCES

[75] Inventors: Ibrahim A. Ismail, South Bend; Teresa Yip, Elkhart, both of Ind.

[73] Assignee: Miles Inc., Elkhart, Ind.

[21] Appl. No.: 819,282

[22] Filed: Jan. 16, 1986

[51] Int. Cl.$^4$ .................... G01N 21/78; G01N 33/52
[52] U.S. Cl. ........................... 436/66; 422/56; 422/57; 427/2; 435/28; 435/805; 436/904
[58] Field of Search ................ 422/56, 57; 436/66, 436/135, 904; 435/28, 805; 427/2

[56] References Cited

U.S. PATENT DOCUMENTS

| | | | |
|---|---|---|---|
| 3,853,471 | 12/1974 | Rittersdorf et al. | 436/66 |
| 3,853,472 | 12/1974 | Rittersdorf et al. | 436/66 |
| 3,975,161 | 8/1976 | Svoboda et al. | 436/66 X |
| 3,986,833 | 10/1976 | Mast et al. | 436/66 |
| 4,447,542 | 5/1984 | Gantzer | 436/66 |
| 4,587,220 | 5/1986 | Mayambala-Mwanika et al. | 422/56 X |

OTHER PUBLICATIONS

Kainoau, Chemical Abstracts, vol. 102, 1985, No. 102:92523y.

*Primary Examiner*—Barry S. Richman
*Assistant Examiner*—Robert J. Hill, Jr.
*Attorney, Agent, or Firm*—Konrad H. Kaeding; Mary G. Boguslaski

[57] ABSTRACT

A stable test device for the determination of a peroxidatively active substance comprising a carrier containing 1,4-diisopropylbenzene dihydroperoxide and a benzidine indicator in a molar ratio of from 0.9 to 3.0. The composition can be incorporated in a carrier matrix along with a ferric chelate to provide ascorbate resistance thereto, which is important in a urine test for occult blood. The test device is stable under storage and heat stress and can be used to prepare a multitest strip containing a glucose test based on a peroxidase/potassium iodide indicator system.

14 Claims, No Drawings

STABLE COMPOSITION FOR THE DETERMINATION OF PEROXIDATIVELY ACTIVE SUBSTANCES

I. FIELD OF THE INVENTION

The invention relates to stable compositions for the determination of peroxidatively active substances in aqueous fluids in general and to stable test devices for occult blood in urine in particular.

II. UTILITY

Hemoglobin and its derivatives are typical examples of "peroxidatively active" substances because they behave in a manner similar to the enzyme peroxidase. Such substances have also been referred to as pseudoperoxidases, i.e., enzyme-like in that they catalyze redox reactions between peroxides and such indicator compounds as benzidine; o-tolidine; 3,3',5,5'-tetramethylbenzidine; 2,7-diaminofluorene or similar substances, thereby producing a color change. Tests for peroxidatively active substances are particularly useful for detecting low levels of blood, often termed "occult" blood, in body fluid samples such as urine or feces. The presence of blood in urine or feces is indicative of bleeding which can be caused by a variety of abnormal conditions including cancer. Because it is important to diagnose such conditions early, occult blood tests are usually included on test devices composed of multiple test pads, each pad containing reagents suitable for testing a different analyte, referred to herein as multiple test devices or "multiples", which are used to screen urine samples during routine physical exams. Also commonly included in most multiple test screening devices is a peroxidase-based glucose determination.

A problem has been observed when a glucose test using potassium iodide indicator system is placed on a multiple with an occult blood test containing a hydroperoxide as a substrate, and the resulting multiples are bottled, stored and/or shipped. Hydroperoxides commonly used in these tests, particularly cumene hydroperoxide, 2,5-dimethylhexane-2,5-dihydroperoxide and p-t-butylcumene hydroperoxide, apparently volatilize and/or decompose during storage and handling; and react with the potassium iodide in the glucose test causing "greening" or a false positive reaction while sealed in the bottle. This invention has solved that problem.

III. INFORMATION DISCLOSURE

Occult blood tests are well known in the art and are generally based on the use of a hydroperoxide as a substrate for hemoglobin, a chromogen and a stabilizer or accelerator for the reaction.

U.S. Pat. No. 3,853,471 claims a test strip composed of a carrier containing a hydroperoxide, a chromogen and a phosphoric acid or phosphonic acid amide as a stabilizer. Diisopropyl benzene dihydroperoxide is disclosed as one useful substrate.

U.S. Pat. No. 3,975,161 claims a test strip composed of a bibulous carrier impregnated with a composition containing an organic hydroperoxide or salt thereof, an acid buffer, a chromogen, a wetting agent, a solid polymeric film-forming natural or synthetic substance and a novel accelerator. The accelerator is isoquinoline or one of its derivatives. It is claimed that the hydroperoxide can be selected from the group consisting of cumene hydroperoxide; para-methane hydroperoxide; 1,4-diisopropylbenzene-1,4-dihydroperoxide; 2,5-dimethylhexane-2,5-dihydroperoxide or 1-hydroxycyclohexane-1-hydroperoxide.

The acid salts or adducts of quinoline and its derivatives have been claimed in U.S. Pat. No. 3,986,833 as potentiating agents in test compositions for the detection of peroxidatively active substances.

IV. SUMMARY OF THE INVENTION

The invention provides a stable test composition for the determination of a peroxidatively active substance in sample, comprising: 1,4-diisopropylbenzene dihydroperoxide and a benzidine indicator in a molar ratio of from about 0.9 to about 3.0.

A stable test device, sensitive to the presence of one part occult blood in one million parts of a urine sample is formed with a carrier matrix incorporated with a test composition which additionally includes an enhancer and a buffer capable of providing a pH in the range from about 4 to 7.5. Ascorbate acid resistance can be imparted to the test device by the inclusion of a ferric chelate. The device can be used for the preparation of a multiple which is also capable of the determination of glucose based on the use of glucose oxidase, peroxidase and a potassium iodide indicator without any evidence of a greening problem.

V. DESCRIPTION OF THE INVENTION

The stable composition of the invention can be used to determine the presence of peroxidatively active substances in a sample. Any aqueous fluid sample, or sample dissolvable in an aqueous fluid, suspected to contain a peroxidatively active substance can be tested. The test composition is particularly useful with body fluids such as urine or excreta. One of the most useful embodiments is a solid state test device for occult blood, designed for use in urine. The urine occult blood test is particularly useful as one reagent pad on a multiple test device. Such multiple test devices usually also include at least a glucose determination. A variety of multiples are available from Ames Division of Miles Laboratories, Inc., Elkhart, IN., under the MULTISTIX ® reagent strip and N-MULTISTIX ® reagent strip trademarks.

THE PROBLEM

Previous MULTISTIX ® and N-MULTISTIX ® formulations including both a glucose determination and an occult blood test have been found to exhibit a phenomenon known as "greening" of the glucose reagent pad during shipment and/or storage prior to consumer use. The glucose determination is based on the generation of hydrogen peroxide by glucose oxidase after contact with a glucose containing sample, and subsequent determination of the hydrogen peroxide generated, by a potassium iodide indicator system in the presence of peroxidase to form a visible color. The "greening" of the glucose pad indicated that some reaction with the peroxidase/potassium iodide system had taken place even before the consumer opened the bottle of reagent strips for use. It was believed that this phenomenon was caused by decomposition and/or volatilization of the organic hydroperoxide substrate in the occult blood test on the multiple during storage and shipping.

Commercial sale of such multiples requires sufficient shelf life to allow for shipment, distribution and an adequate use life for the customer. The "greening" could be taken to indicate a positive response of 30 milligram per deciliter (mg/dL) glucose in a sample which should have given a negative response. Therefore, such "greening" prior to use is unacceptable.

THE SOLUTION

A clinically useful occult blood test should have a sensitivity of 1 part hemoglobin (occult blood) in one million parts of urine. Only one hydroperoxide was found which provided sufficient sensitivity, stability and did not affect other reagent tests on a multiple test device: 1,4-diisopropylbenzene dihydroperoxide.

1,4-diisopropylbenzene dihydroperoxide (abbreviated DBDH and referred to as "the dihydroperoxide" herein, which can also be named α,α'-dihydroperoxy-1,4-diisopropylbenzene) has the formula:

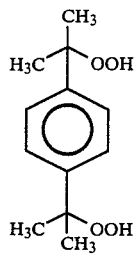

DBDH was found to be a nonvolatile, nonsublimable compound. Unlike other hydroperoxides, it was found to be nonexplosive under various conditions and could therefore be manufactured and stored in bulk.

Optimization of a test device formulation for the determination of occult blood in urine using 3,3',5,5'-tetramethylbenzidine, showed that a critical molar ratio must be maintained between the dihydroperoxide and the benzidine indicator to achieve the desired response. The critical molar ratio was from about 0.9 to about 3.0 moles of dihydroperoxide per mole of benzidine indicator, preferably about 1.6 to 3.0 moles dihydroperoxide per mole of benzidine indicator. Below this molar ratio range, the requisite sensitivity was not achieved; above this molar ratio, the reagent pad surprisingly exhibited no apparent reactivity to hemoglobin.

Test Composition

A stable test composition for the determination of a peroxidatively active substance requires the same critical molar ratio of the dihydroperoxide to benzidine indicator. The composition is stable, i.e., retains activity, to heat stress conditions of 4 weeks at 50° C. Although 3,3',5,5'-tetramethylbenzidine is a preferred indicator, other benzidine indicators can also be used. Suitable benzidine indicators include tetraethylbenzidine, o-tolidine, benzidine, o-dianisidine and the like.

A sensitivity of one part peroxidatively active substance per one million parts sample is obtained by including an enhancer in the composition. Enhancers, known in the art for the determination of peroxidatively active substances, can be used. These include quinolines and their derivatives and isoquinolines and their derivatives. The enhancer preferably can be isoquinoline, 4-bromoisoquinoline, 4-methylquinoline, 6-methoxyquinoline, 3-aminoquinoline or 5,6-benzoquinoline. The quinolines, 4-methylquinoline and 6-methoxyquinoline, are preferred in this group; 4-methylquinoline (available under the trademark Lepidine® from Aldrich Chemical Co., Milwaukee, WI) being the most preferred.

The test composition should be buffered if the test sample is very acidic or very basic. The buffer can be chosen from any of those which is capable of providing a pH in the pH range of from about 4.0 to about 7.5. Buffers such as phosphate, citrate and the like, or combinations thereof, can be used to provide the appropriate pH range.

Test Device

The test compositions described above can be incorporated into a carrier matrix and dried to provide a convenient dry reagent test format.

The test device is a particularly convenient format for screening body samples. A stable test device sensitive to the presence of at least one part hemoglobin per million parts of a body sample can be prepared by incorporating a carrier matrix with DBDH and a benzidine indicator in a molar ratio of from about 0.9 to about 3.0, an enhancer and a buffer capable of providing a pH in the range of from about 4 to 7.5. Useful benzidine indicators, enhancers and buffers have been described previously. A stable test device is defined by the ability of the device to provide a correct test result after storage at 50° C. for 4 weeks. A visually read test result is said to be correct if the color response is not judged to be different from the original color block response. This is sometimes termed "less than one half color block decrease in color" and refers to the color blocks on an appropriate chart provided to the user. A color response within "one half color block" of the color is read as the correct level of analyte. The sensitivity useful for clinical screening for hemoglobin (occult blood) has been determined to be 1 part per million. Body fluid samples commonly have a pH not within the desired range and therefore a buffer is added to the test composition.

A commercially feasible urine occult blood test device must have three principal attributes: stability, sensitivity and resistance to ascorbic acid affects. Stability and sensitivity requirements have been defined. A sensitivity of 1:1,000,000 is equivalent to 0.15 mg hemoglobin per deciliter urine. Ascorbic acid affects are well known in the art. Ascorbic acid will interfere with the oxidation of the indicator and will produce apparent negative results. "Ascorbate resistance" is defined herein to mean negligible interference with the indicator color observed if a urine sample contains as much as 50 milligrams ascorbic acid per deciliter of sample. Ascorbic acid or ascorbate are common interferents with diagnostic tests based on redox indicator systems and are particularly important when testing a population which routinely ingests Vitamin C.

Resistance to ascorbate interference can be imparted to the test device by the addition of ferric chelates to the test composition. Ferric chelates which can be used include ferric polycarboxyalkyl amine chelates such as ferric chelates of N-(2-hydroxyethyl)ethylenediamine triacetic acid (Fe-HEDTA), ethylenediamine tetraacetic acid (Fe-EDTA), cyclohexylene diaminetetraacetic acid (Fe-CDTA), nitrilotriacetic acid (Fe-NTA), iminodiacetic acid (Fe-IMDA), ethylenediaminediacetic diproprionic acid (Fe-EDDP both α and β forms), hydroxyethyliminodiacetic acid (Fe-HIMDA) and mixtures thereof. Preferred are Fe-HEDTA and Fe-EDTA; most preferred is Fe-HEDTA. The ferric polycarboxyalkyl amine chelates are described more fully in U.S. Pat. No. 4,587,220, which is incorporated herein by reference.

In order to use Fe-HEDTA to provide desired ascorbate resistance, the test device is preferably buffered above pH 6.5, i.e., 6.5 to 7.1. It was found with extensive experimentation that a optimal pH range of 6.7 to 7.1, most preferably 6.80 to 6.82, provided the best balance of sensitivity, stability and ascorbate resistance with urine samples which exhibit highly variable pH and specific gravity. Of the over two hundred and fifty buffer combinations tried, a combination of tris-(hydroxymethyl)aminomethane-malonic acid and triethanolamine borate in a molar ratio of 1 to 3 was found to give optimum results for urine testing. Other buffers and buffer combinations, such as phosphate, citrate or succinate, can be used. However, some sacrifice in sensitivity, stability or ascorbate resistance must then be made.

Other components such as thickeners, color stabilizers, surfactants or the like can be added. The addition of a polymer such as polyvinylpyrrolidone increases stability and the uniformity of color formation on the test device.

Carrier Matrix

The carrier matrix can be any substance capable of being incorporated with the components of the test composition, as long as it is substantially inert with respect to the test composition, porous and/or absorbent relative to the aqueous sample to be tested. The expression "carrier matrix" refers to either bibulous or nonbibulous matrices which are insoluble in and maintain their structural integrity when exposed to water or to other physiological fluids. Suitable bibulous matrices which can be used include paper, cellulose, wood, synthetic resin fleeces, woven and nonwoven fabrics and the like. Paper is a preferred carrier matrix. Nonbibulous matrices includes glass fiber, polymer films, preformed or microporous membranes and organoplastic materials, such as polypropylene and the like.

Incorporation can be accomplished by any method such as dipping, spreading or spraying. A preferred method is impregnation of the paper by dipping in a reagent solution and drying to remove solvent. Drying can be accomplished by any means which will not deleteriously affect the reagents incorporated, usually by means of an air drying oven.

Method of Preparation

Previous occult blood tests were prepared by incorporating a carrier matrix with a single solution containing all the test ingredients and drying the matrix. Commonly a paper carrier was incorporated by dipping the paper into a reagent containing solution. The method can still be used to prepare a test device for the determination of a peroxidatively active substance in general. However, the preferred test device, which includes Fe-HEDTA as the ferric chelate, should be prepared by two step incorporation process.

The method of preparing the preferred test device includes the following steps:

(a) preparing a first solution containing a ferric chelate capable of imparting ascorbate resistance to the test device and a buffer capable of providing a pH in the range of from about 6.5 to about 7.1, (b) preparing a second solution containing organic solvent, 1,4-diisopropylbenzene dihydroperoxide and a benzidine indicator in a molar ratio of from about 0.9 to 3.0 and an enhancer;

(c) incorporating a carrier matrix with the first or second solution;

(d) drying the incorporated carrier;

(e) incorporating the dried carrier with the other of the first or second solutions not previously incorporated; and (f) drying the doubly incorporated carrier.

The first solution contains less than 50% of an organic solvent, while the second solution contains more than 50% organic solvent, preferable to 70 to 80%. Suitable organic solvents for either incorporation step include dimethylformamide, ethanol and methoxypropanol.

A preferred range for the molar ratio of DBDH to benzidine is 1.6 to 3.0. The molar ratios given for DBDH to benzidine indicator were calculated from the amount of compounds used to make the second incorporating solution. The molar ratio on the dried test device can be slightly lower due to the loss of a small amount (approximately 10%) of DBDH, due to decomposition, during drying of the paper. Additional components, such as polyvinylpyrrolidone, can be incorporated in whichever solution is most convenient.

The resultant doubly dried and incorporated paper is cut and affixed to a rigid polymer backing such as polystyrene. Other backing materials are well known in the art. The resulting test device is composed of a small rectangular reagent pad affixed to a water impervious handle for convenience. In a multiple test device, other reagent pads containing a variety of diagnostic tests such as glucose, protein, pH, specific gravity and leukocytes can be added. In particular, the reagent pad of this invention can be used in a multiple test device with a glucose reagent pad containing peroxidase/potassium iodide indicator system.

Use

The test compositions can be used by forming a solution either directly with an aqueous test sample or by the addition of water prior to contact with a sample. The test device is advantageously used by contacting a body fluid sample, removing the device and determining the color developed either visually or instrumentally. Visually read tests usually provide a semiquantitative concentration range upon comparison to an appropriate color chart provided to the user. Instrumental results are somewhat more quantitative and can be obtained with an instrument such as the CLINITEK ® 10 reflectance photometer availavle from Ames Division, Miles Laboratories, Inc., Elkhart, IN. Results for an occult blood test dipped into a urine sample are usually available in less than about one minute for visual or instrumental reading. Instrumental reading of a multiple may take longer due to the inclusion of other reagent test with longer read times.

VI. ABBREVIATIONS AND SOURCES

The following abreviations are used for convenience. Sources of chemicals used in the Examples (Section VII) are as indicated.

| | |
|---|---|
| M | molar |
| mM | millimolar |
| mg | milligrams |
| dL | deciliter |
| DBDH | 1,4-diisopropylbenzene dihydroperoxide |
| % | percent, volume per volume unless otherwise indicated |
| °C. | degrees centigrade |
| PVP K30 | polyvinylpyrrolidone molecular weight 40,000 available from |

| | -continued |
|---|---|
| | GAF Corp. New York, N.Y. |
| Lepidine | 4-methylquinoline available from Aldrich Chemical Co., Milwaukee, WI. |
| SSD | Standard Solution Designated Unit |
| Fe—HEDTA | Ferric N—(2-hydroxyethyl) ethylenediamine triacetic acid |
| SG | Specific Gravity |
| Tris | Tris(hydroxymethyl)aminomethane |
| Bis-Tris | 1,3-bis[tris(hydroxymethyl)methylamino]propane |
| HEPES | N—2-hydroxyethylpiperazine-N'—2-ethane-sulfonic acid |
| TEB | triethanolamine borate |
| Tris-maleate | tris(hydroxymethyl)aminomethane-maleic acid |
| Tris-malonate | tris(hydroxymethyl)aminomethane-malonic acid |

The following examples describe experiments which were performed. While the examples serve to illustrate the invention they are not to be interpreted as limiting in scope, which is defined solely by claims. On skilled in the art will be able to make such variations, substitutions and changes in the components of the composition and reaciton parameters as may seen desirable.

VII. EXAMPLES

EXAMPLE 1

Preferred Embodiment

A stable, ascorbate resistant test sensitive to the presence of one part occult blood to one million parts of a urine sample, was prepared in a two step impregnation process as follows.

The first impregnation solution contained an aqueous mixture of the following:

| | |
|---|---|
| tris-malonate | 0.1 M |
| triethanolamine borate | 0.3 M |
| sodium dodecyl sulfate | 0.3% by weight |
| Fe—HEDTA | 5 mm | adjusted to a pH between 6.80 and 6.82 and subsequently diluted with diethylformanide (final solution contained 45% diethylformamide). Whatman ® 3MM paper was dipped into the aqueous solution and dried for five minutes at 86° C.

The dried paper was then dipped into a second impregnation solution containing:

| | |
|---|---|
| 3,3',5,5'-tetramethylbenzidine | 25 to 35 mM |
| 4-methylquinoline | 0.6% by volume |
| PVP K30 | 4% by weight |
| DBDH | 45 to 60 mM |
| dimethylformamide | 80% by volume |
| ethyl orange | 25 mg/dL |
| orange G dye | 25 mg/dL |

Testing showed that this formulation met all the requirements for a commercially feasible urine occult blood test.

EXAMPLE 2

Unsuitable Hydroperoxides

Table I below shows a number of other hydroperoxides which were used in place of DBDH in the formulation of Example 1 and found to be unsuitable.

TABLE I

| Hydroperoxide | Comments |
|---|---|
| cumene hydroperoxide | Reactive but turns glucose test green on multiple |
| 1,4-diisopropylbenzene monohydroperoxide | Reactive but turns glucose test green on multiple |
| p-t-butylisopropyl benzene hydroperoxide | Reactive but turns glucose test green on multiple |
| 2,5-dimethylhexane-2,5-dihydroperoxide | Reactive but turns glucose test green on multiple |
| 2-(α-hydroperoxyisoproyl) 6-isopropylnaphthalene | Low reactivity |
| 2,6-di-(α-hydroperoxyisopropyl)naphthalene | Unreactive |
| p-(α-hydroperoxyisopropyl) benzoic acid | Unsuitable, reactive even in the absence of Blood (False Positive Results) |
| p-isopropyl benzene sulfonic acid hydroperoxide | Unreactive |

EXAMPLE 3

Unsuitable Buffers

The buffer system was found to be important to provide a commerically feasible dry reagent urine occult blood test device which has resistance to the affects of urine pH and specific gravity as well as the other characteristics required. Testing was done with a single pad test device for urine occult blood uring the formulation of Example 1 with variations in the buffer. The following table provides a partial list of buffer combinations tried with a DBDH/Fe-HEDTA test formulation impregnated into a paper carrier.

TABLE 2

| Buffer Systems | |
|---|---|
| Buffer System | Result |
| Bis-Tris, pK 6.5 | Not resistant to pH or SG variations of urine |
| HEPES, pK 7.6 | Strip not reactive indicator reacted during manufacture |
| Imidazole, pK 7.0 | not reactive to hemoglobin |
| Imidazole with Tris (pK 8.3) | indicator reacted during manufacture not reactive to hemoglobin |
| Phosphate, pK 6.9 | ascorbate resistance requirements not met |
| Citrate with Phosphate | ascorbate resistance requirements not met |
| Tris with Maleate (pK$_2$ = 6.2) | ascorbate resistance requirements not met, poor performance with pH/SG variations |
| Maleate with TEB | paper spotted |
| Tris/Maleate/TEB | stability requirements not met |
| Malonate/TEB (no Tris) | Lost ascorbate resistance after stress |

TABLE 2-continued

| Buffer System | Result |
| --- | --- |
| | treatment |
| Citric acid - Sodium citrate | Ascorbate |
| Triethanolamine Borate, | resistant |
| pH = 6.5 | pH/SG resistant |
| | but shows false |
| | positives |
| 0.1 M Tris/Malonate | Best combination |
| 0.3 M TEB pH 6.8 | possible for this |
| | system |
| 0.2 M citrate | No buffering |
| 0.3 M TEB pH 7.1 | capacity at pH |
| 45% ethanol | greater than 7.0 |
| 0.1 M Tris/Citrate | No buffering |
| 0.3 M TEB pH 7.1 | capacity at pH |
| | greater than 7.0 |

It was found that the buffer system tris-malonate, triethyanolamine borate in a molar ratio of 1 to 3 provided the best results for a clinical urine population which contains a wide range of pH and specific gravity variations, which variations affect the sensitivity of the test.

EXAMPLE 4

Stability

The preferred test device formulation of Example 1 was used in the following experiments to prove the unique heat stable characteristics of the test device. The stability data shown below (Table II) compares the HEMASTIX ® reagent test strip, an occult blood test available commercially from Ames Division, Miles Laboratories, Inc., Elkhart, IN., with the test device of the present invention. Readings for the present test device after heat stress for four weeks at 50° C. were very close to the expected value, while HEMASTIX ® readings for higher blood levels were consistently low.

TABLE II

| Blood Level | 4 Weeks at 50° C. | | Expected |
| --- | --- | --- | --- |
| (mg/dL) | Hemastix | Present Test | (SSD Units) |
| 0 | 10 | 10 | 10 |
| 0.018 | 10 | 18 | 20 |
| 0.045 | 18 | 28 | 30 |
| 0.135 | 29 | 38 | 40 |

SSD units are an arbitary set of units used for different color block levels, where negative is read as 10 and progressive levels increase by 10 units.

EXAMPLE 5

Greening

One of the problems in quantifying results for visually read tests is the variability in color vision among individuals. This variability can be eliminated with the use of a MacBeth 1500 Colorimeter available from Kollmorgen Corp., Newburgh, N.Y. which measures the color in terms of a three dimensional scale $L^*$, $a^*$, $b^*$. $L^*$, $a^*$, $b^*$ values allow the unambiguous description of color. Similar colors have equivalent values, and a difference in one or more of these values indicates a difference in color.

The occult blood test on a multiple test device, available commercially as N-MULTISTIX ® SG from Ames Division, Miles Laboratories, Inc., Elkhart, IN, was read on the MacBeth after reaction with a control sample, as were strips subjected to heat stress at 60° C. and tested at 3 and 7 day intervals. Plots of the $L^*$, $a^*$, $b^*$ values obtained showed a definite shift toward the next higher color block. After heat stress, the strip color after dipping in a negative sample was closer to the expected color for a 30 mg/dL hemoglobin sample than to a negative sample. Likewise the color for a 30 mg/dL sample showed an appreciable shift toward the color expected from a 100 mg/dL sample.

Similar plots performed with a multipad strip containing the same glucose test as used previously (glucose oxidase, peroxidase and potassium iodide) and the occult blood test of the present invention, showed essentially no shift on the $L^*$, $a^*$, $b^*$ axes when tested at room temperature and after heat stress at 60° C. for 7 days. In spite of the rigorous heat stress applied no "greening" was observed for negative and 30 mg/dL samples.

Modifications and variations of the preferred embodiments can be made without departing from the spirit of the invention.

What is claimed is:

1. A stable test composition for use in determining the presence of peroxidatively active substances in a sample of fluid wherein the composition is typically stable under normal ambient conditions and will not adversely affect the usefulness of a peroxidase and potassium iodide based substance for glucose determination if such a peroxidase and potassium iodide based substance and said test composition are supported on the same diagnostic test strip means or are otherwise stored or used in the presence of one another, said test composition comprising:
   (a) 1,4-diisopropylbenzene dihydroperoxide; and
   (b) a benzidine indicator in a molar ratio (dihydroperoxide: indicator) in the range of about 0.9 to about 3.

2. The composition of claim 1 wherein said indicator comprises 3,3′, 5,5′-tetramethylbenzidine.

3. The composition of claim 1 further comprising an enhancer.

4. The composition of claim 3 wherein said enhancer comprises 4-methylquinoline or 6-methoxyquinoline.

5. The composition of claim 4, further comprising a buffer sufficient to provide the composition with a pH in the range of from about 4 to about 7.5.

6. A stable test device capable of determining the presence of at least one part hemoglobin in one million parts of a body sample without adversely affecting a potassium iodide based glucose test if such a potassium iodide based glucose test is stored or used in the presence of, or as part of, said test device, said test device comprising:
   (a) a carrier matrix; and
   (b) a test composition incorporated therein comprising 1,4-diisopropylbenzene dihydorperoxide and a benzidine indicator in a molar ratio (dihydroperoxide indication) in the range of from about 0.9 to about 3.

7. The test device of claim 6 wherein said indicator comprises 3,3′,5,5′-tetramethylbenzidine.

8. The test device of claim 6 wherein said test composition further comprises an enhancer.

9. The test device of claim 8 wherein said test composition further comprises a buffer sufficient to provide the composition with a pH in the range of from about 4 to about 7.5.

10. The test device of claim 9 wherein the buffer is a combination of tris(hydroxymethyl)aminomethane-malonic acid and triethanolamine borate, in a molar ratio of about 1 to 3.

11. The test device of claim 9 whrein said test compostion further comprises a ferric chelate in an amount sufficient to provide ascorbate resistance to the test compostion.

12. The test device of claim 11 wherein the ferric chelate is the ferric chelate N-(2-hydorxyethyl)ethylene-diamine triacetic acid, and the buffer is sufficient to provide the composition with a pH in the range of from about 6.5 to about 7.1.

13. The test of claim 12 wherein said test composition further comprises polyvinylpyrrolidone.

14. A method of preparing a stable, ascorbate resistant test device which is sensitive to the presence of at least one part hemoglobin per million parts of a body fluid sample, comprising the steps of:
   (a) preparing a first solution containig a ferric chelate capable of imparting ascorbate resistance to the test device and a buffer sufficient to provide a pH in the range of from about 6.5 to about 7.1;
   (b) preparing a second solution containing an organic solvent, 1,4-diisopropylbenzene dihydroperoxide and a benzidine indicator in a molar ration (dihydroperoxide: indicator) of from about 1.6 to 3. and an enchancer;
   (c) incorportaitng a carrier matrix with either the first or second solution;
   (d) drying the incorporated carrier;
   (e) incorporating the dried carrier with the other of the first or second solutions, not previously incorporated; and
   (f) drying the doubly incorporated carrier.

* * * * *